United States Patent [19]

Watanabe et al.

[11] Patent Number: 5,491,258

[45] Date of Patent: Feb. 13, 1996

[54] MOLDED CATALYST OR SUPPORTED CATALYST FOR SYNTHESIZING METHACROLEIN AND METHACRYLIC ACID, A PROCESS FOR PRODUCTION THEREOF, AND A PROCESS OF USE THEREOF

[75] Inventors: Seigo Watanabe; Motomu Ohkita, both of Otake, Japan

[73] Assignee: Mitsubishi Rayon Co., Ltd., Tokyo, Japan

[21] Appl. No.: 302,979

[22] Filed: Sep. 12, 1994

Related U.S. Application Data

[63] Continuation of Ser. No. 969,205, filed as PCT/JP92/00730, Jun. 5, 1992, published as WO92/21440, Dec. 10, 1992, abandoned.

[30] Foreign Application Priority Data

Jun. 6, 1991 [JP] Japan .................................... 3-134946

[51] Int. Cl.$^6$ ............................ C07C 51/21; C07C 45/32; B01J 23/881; B01J 33/00

[52] U.S. Cl. .......................... 562/538; 568/476; 568/477; 568/479; 568/480; 428/404; 428/407; 427/228; 427/221; 427/154; 502/205; 502/212; 502/220; 502/218; 502/215; 502/242; 502/243; 502/249; 502/306; 502/307; 502/308; 502/310; 502/311; 502/159; 502/241

[58] Field of Search ....................... 502/159, 307, 502/308, 310, 311, 306, 241, 242, 243, 249, 215, 220, 221, 212, 205, 218; 562/510, 534, 538, 546; 568/471, 477, 479, 480, 476; 427/221, 226, 228; 428/404, 407; 422/213

[56] References Cited

U.S. PATENT DOCUMENTS

| | | | |
|---|---|---|---|
| 4,442,308 | 4/1984 | Arntz et al. | 502/212 X |
| 4,564,607 | 1/1986 | Yoneda et al. | 502/306 X |
| 4,579,689 | 4/1986 | Hershman et al. | 502/158 X |
| 4,689,250 | 8/1987 | Quella et al. | 427/216 |
| 4,946,819 | 8/1990 | Sasaki et al. | 502/249 X |
| 4,956,322 | 9/1990 | Gouzzard et al. | 502/62 |
| 5,166,119 | 11/1992 | Oh-Kita et al. | 502/205 |
| 5,250,485 | 10/1993 | Kuroda et al. | 502/159 |
| 5,276,178 | 1/1994 | Onodera et al. | 562/538 X |
| 5,422,326 | 6/1995 | Kuroda et al. | 502/159 |

FOREIGN PATENT DOCUMENTS

| | | |
|---|---|---|
| 0267556 | 5/1988 | European Pat. Off. . |
| 0311508 | 4/1989 | European Pat. Off. . |
| 53-8390 | 1/1978 | Japan . |
| 56-046832 | 4/1981 | Japan . |
| 57-119837 | 7/1982 | Japan . |
| 59-173140 | 10/1984 | Japan . |
| 2-227140 | 9/1990 | Japan . |
| 3-200733 | 9/1991 | Japan . |
| 4363147 | 12/1992 | Japan . |
| 878730 | 10/1961 | United Kingdom . |
| 2138694 | 10/1984 | United Kingdom . |

OTHER PUBLICATIONS

European Search Report dated May 18, 1993.
Chemical Abstracts, CA 97:181696, JP 57,119,837 (Jul. 26, 1982).

*Primary Examiner*—Douglas J. McGinty
*Attorney, Agent, or Firm*—Armstrong, Westerman, Hattori, McLeland & Naughton

[57] ABSTRACT

For providing a molded catalyst or a supported catalyst which has an excellent mechanical strength and is intended for producing methacrolein and methacrylic acid from isobutylene or tertiary butanol, the surface of a molded catalyst or a supported catalyst which contains molybdenum, bismuth and iron is coated with one or more highly depolymerizable organic high-molecular weight compounds.

When used, the catalyst is packed into a reactor and then heated to remove the organic high-molecular weight compound(s) by depolymerization.

12 Claims, No Drawings

MOLDED CATALYST OR SUPPORTED CATALYST FOR SYNTHESIZING METHACROLEIN AND METHACRYLIC ACID, A PROCESS FOR PRODUCTION THEREOF, AND A PROCESS OF USE THEREOF

This application is a continuation of application Ser. No. 07/969,205 filed as PCT/JP92/00730, Jun. 5, 1992, published as WO92/21440, Dec. 10, 1992, now abandoned.

TECHNICAL FIELD

The present invention relates to a molded catalyst or supported catalyst for synthesizing methacrolein and methacrylic acid which has an excellent mechanical strength, a process for producing the same, and a process for synthesizing methacrolein and methacrylic acid using the catalyst.

BACKGROUND ART

In general, molded catalysts or supported catalysts for industrial use should have a mechanical strength above a certain level so as not to be pulverized or disintegrated during their transportation or packing into a reactor. The mechanical strength of the catalysts can be improved to a certain extent by controlling the molding pressure or devising a molding or supporting procedure. The catalysts having a mechanical strength increased by such a method, however, are generally disadvantageous in that the yield of a desired product is low for reasons such as the decreased specific surface area of the catalysts, the decreased number of active sites effective for reaction, and the uncontrollableness of the pore distribution effective for reaction.

For the above purpose, several methods have been proposed. For example, Japanese Patent Unexamined Publication No. 57-119837 has proposed a process for obtaining a catalyst having a certain measure of mechanical strength and capable of giving a high yield of a desired product, by adding an organic high-molecular weight compound such as a cellulose, a polyvinyl alcohol or a polyethylene glycol at the time of molding a catalyst for oxidation of olefins. In this patent, there is used a method which comprises mixing a precursor of catalyst with said organic high-molecular weight compound, molding the mixture, and calcining the resulting molded product in an oxygen-containing atmosphere at a temperature of 400°–700° C., preferably 500°–650° C. to remove said organic high-molecular weight compound. The organic high-molecular weight compounds have such a low depolymerizability that they are hardly decomposed at about 400° C. Therefore, in order not to employ a very high temperature and a very long time for removal, the organic high-molecular weight compound should be removed by combustion in an oxygen-containing atmosphere at a high temperature. In this case, it is appreciated that the catalyst is deactivated by the generation of heat by the combustion, and hence a very difficult procedure is required. In addition, in said patent, there is employed a method which comprises removing said organic high-molecular weight compound added to the catalyst molded product, by calcining, packing the resulting molded catalyst into a reactor, and carrying out a reaction. In order that the molded catalyst freed of said organic high-molecular weight compound may have a mechanical strength enough to withstand the packing, it is necessary to set the molding pressure at the time of molding at a fairly high value. In general, when the mechanical strength of a molded catalyst or a supported catalyst is increased by raising the molding pressure or the supporting pressure, the yield of a desired product is generally often lowered for reasons such as the decreased specific surface area of the catalyst, the decreased number of active sites effective for reaction, and the uncontrollableness of the pore distribution effective for reaction. Therefore, it is not desirable.

The specification of British Patent Laid-Open No. 2138694, which is equivalent to U.S. Pat. No. 4,564,607, has reported a method for increasing the mechanical strength by using a whisker as a support-reinforcing agent in the production of a supported catalyst. However, also in the method of this patent, a carrier itself is required to have a mechanical strength enough to withstand transportation, packing, etc. Therefore, it is necessary to set the supporting pressure at the time of supporting at a fairly high value. Consequently, said method is disadvantageous in that the yield of a desired product tends to be lowered.

On the other hand, the present invention is a molded catalyst or a supported catalyst in which the surface of at least a portion of the molded catalyst or the supported catalyst has been coated with one or more highly depolymerizable organic high-molecular weight compounds in an amount of 0.1 to 40% by weight based on the weight of said catalyst. Furthermore, the present invention is a process which comprises packing the coated catalyst into a reactor, removing said organic high-molecular weight compound(s) by depolymerization before the initiation of a reaction, and then carrying out the reaction. The present invention can be said to be substantially different from the above patents in that in the present invention, it is not necessary to increase the molding pressure or the supporting pressure at the time of molding or the time of supporting unnecessarily.

DISCLOSURE OF THE INVENTION

The present invention is intended to provide a molded catalyst or supported catalyst for synthesizing methacrolein and methacrylic acid which has such an excellent mechanical strength that the molded catalyst or the supported catalyst is hardly pulverized or disintegrated during packing or transportation; a process for production thereof; and a process for synthesizing methacrolein and methacrylic acid using the catalyst.

One aspect of the invention is directed to a molded catalyst or supported catalyst for synthesizing methacrolein and methacrylic acid comprising a catalytic substance for synthesizing methacrolein and methacrylic acid by vapor phase catalytic oxidation of isobutylene or tertiary butanol with molecular oxygen, which is characterized in that the surface of at least a portion of the molded catalyst or the supported catalyst has been coated with one or more highly depolymerizable organic high-molecular weight compound(s). Another aspect of the invention is directed to a process for production of said catalyst. Furthermore, still another aspect of the invention is directed to a process for producing methacrolein and methacrylic acid using said catalyst.

BEST MODE FOR CARRYING OUT THE INVENTION

Although the shape of the molded catalyst used in the present invention is not critical, it is usually a spherical shape, columnar shape, cylindrical shape, confeitos-like shape or the like, and there are used molded catalysts obtained by molding by the use of a tableting machine, extruder, tumbling granulator, etc. Although the supported catalyst is not limited in the kind of its carrier, those obtained by the use of a conventional carrier of silica, alumina, silica-alumina, magnesia, titania or the like are preferable. The shape of the supported catalyst is not critical and there may be employed any of a spherical shape, columnar shape, cylindrical shape, plate shape, etc.

The catalyst of the present invention can be obtained by coating the surface of at least a portion of the aforesaid shaped catalyst or supported catalyst with one or more highly depolymerizable organic high-molecular weight compounds. As a result of the coating, the mechanical strength of the catalyst is greatly improved, so that there can be markedly prevented the pulverization and disintegration of the catalyst during usual operations and procedures such as the transportation of the catalyst and its packing into a reactor. The organic high-molecular weight compound(s) attached as a coating can easily be removed from the catalyst by decomposition by heating, or combustion. Therefore, a stable catalytic capability can be obtained without any influence of the high-molecular weight compound(s) attached as a coating, by removing the high-molecular weight compound(s) attached as coat, before the initiation of the reaction.

As the high-molecular weight compound(s) used for the coating in the present invention, one or more highly depolymerizable substances are preferably used when there is considered the efficiency of a step of removal thereof by heating at the time of using the catalyst. In general, thermal decomposition of a high-molecular weight compound requires a considerably high temperature. On the other hand, it is well known that when a high-molecular weight compound is burned in the presence of oxygen, generation of a large amount of heat occurs, lowers catalytic activity, and in some cases, injures a catalyst itself. However, since the highly depolymerizable high-molecular weight compound is decomposed into a monomer at a relatively low temperature to be vaporized and evaporated, it does not generate heat, so that a product having a high catalytic activity can be obtained without exposing a catalyst to high temperatures. That is, a procedure of removing the high-molecular weight compound by heating can be more safely carried out for the catalyst.

Preferably, the reduction-by-half temperature (as hereinafter defined) of the highly depolymerizable organic high-molecular weight compound(s) in thermal decomposition in a vacuum is lower than 400° C. The monomer yield in this case is 30% or more.

As high-molecular weight compounds having a relatively high depolymerizability, polystyrenes, poly-α-methylstyrenes, polymethyl methacrylates, polyisobutyl methacrylates, etc. are preferable. Polystyrenes and polymethyl methacrylates are particularly preferable. That is, high-molecular weight compounds which are not expensive and easily soluble in solvents harmless to the catalyst, are preferable. Such compounds may be used singly or as a mixture thereof. Of the above high-molecular weight compounds, main ones have the following characteristics:

| | Thermal decomposition in a vacuum | |
|---|---|---|
| | Reduction-by-half temperature (°C.) | Monomer yield (%) |
| Polystyrene | 364 | 40.6 |
| Poly-α-methylstyrene | 287 | 100 |
| Polymethyl methacrylate | 327 | 91.4 |

The term "reduction-by-half temperature" in the thermal decomposition in a vacuum of the organic high-molecular weight compounds means a temperature at which their weight is reduced by half by heating for 30 minutes, and the term "monomer yield" means the proportion of a monomer in the decomposition product.

In the present invention, the amount of the organic high-molecular weight compound(s) used as a coating is suitably 0.1 to 40% by weight based on the weight of the molded catalyst or the supported catalyst. When the amount is too small, the strength-improving effect is lowered. Coating in a large amount beyond the above range is economically disadvantageous.

In the present invention, in coating the molded catalyst or the supported catalyst with the high-molecular weight compound(s), the coating procedure can be carried out easily and uniformly when there is employed a method which comprises adhering a solution of said high-molecular weight compound(s) in a solvent to said molded catalyst or said supported catalyst in the form of spray or by immersion of said molded catalyst or said supported catalyst in said solution, and then vaporizing and evaporating the solvent. In this case, when the concentration of the organic high-molecular weight compound(s) in the solution is too high, the viscosity of the solution becomes so high that pieces of the molded catalyst or the supported catalyst adhere to one another, resulting in difficulty in operations. Therefore, the concentration of the organic high-molecular weight compound(s) in the solution is preferably in the range of 1 to 30% by weight.

As the catalyst used in the present invention, there is preferably used a catalyst having a composition represented by the general formula:

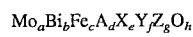

$$Mo_aBi_bFe_cA_dX_eY_fZ_gO_h$$

wherein Mo, Bi, Fe and O denote molybdenum, bismuth, iron and oxygen, respectively; A denotes nickel and/or cobalt; X denotes at least one element selected from the group consisting of magnesium, zinc, manganese, tin and lead; Y denotes at least one element selected from the group consisting of phosphorus, boron, sulfur, tellurium, silicon, selenium, germanium, tungsten and antimony; Z denotes at least one element selected from the group consisting of potassium, sodium, cesium, rubidium and thallium; and a, b, c, d, e, f, g and h denote atomic ratio values for the individual elements: in the case of a being 12, $0.1 \leq b \leq 5$, $0.1 \leq c \leq 5$, $1 \leq d \leq 12$, $0 \leq e \leq 5$, $0 \leq f \leq 5$, $0.01 \leq g \leq 3$, and h being a number of oxygen atoms which is necessary for giving the above valences of the individual constituents.

In the present invention, although materials for the elements as the constituents of the catalyst are not critical, there are usually used oxides, or chlorides, sulfates, nitrates, carbonates, ammonium salts or mixtures thereof which can be converted into oxides by intense heating.

The catalyst of the present invention has an excellent mechanical strength, and very rarely undergoes pulverization, disintegration, etc. during its handling including transportation and packing into a reactor, and when the catalyst is used in the practical reaction, the organic high-molecular weight compound(s) attached as a coating is removed by depolymerization or the like and hence exerts no undesirable influence at all.

A specific example of process for synthesizing methacrolein and methacrylic acid from isobutylene or tertiary butanol by the use of the catalyst of the present invention is a process comprising packing a reactor with a molded catalyst or a supported catalyst which comprises at least molybdenum, bismuth and iron and in which the surface of at least a portion of the molded catalyst or the supported catalyst has been coated with one or more organic high-molecular weight compounds with a high depolymerizability in an amount of 0.1 to 40% by weight based on the weight of said catalyst; subjecting isobutylene or tertiary butanol to vapor phase catalytic oxidation with molecular oxygen by the use of the catalyst which has been freed of said organic high-molecular weight compound(s) by depolymerization before the initiation of the reaction; and thereby synthesizing methacrolein and methacrylic acid.

More concrete explanation is given below. From the catalyst of the invention for which the present application is filed, the organic high-molecular weight compound(s) added to form a coating is removed by heat treatment preferably at a temperature of lower than 400° C. whereby the catalyst is activated.

The catalyst of the invention for which the present application is filed is used for subjecting isobutylene or tertiary butanol to vapor phase catalytic oxidation with molecular oxygen. In this case, the molar ratio of isobutylene or tertiary butanol to oxygen is preferably 1:0.5–3. The starting gas is used preferably after being diluted with an inert gas. Although employment of air as oxygen source is economical, air enriched with pure oxygen may also be used if necessary. The reaction pressure is preferably atmospheric pressure to several atmospheres. The reaction temperature is preferably 250°–450° C. The reaction can be carried out either on a fixed bed or on a fluidized bed.

EXAMPLES

Specific examples of the present invention are explained below by taking the case of packing into a reactor by dropping.

Parts in the examples and comparative examples described below are by weight.

The rate of pulverization by dropping and the rate of shape change of a molded catalyst or a supported catalyst at the time of packing are given by the equations shown below. Pieces of the catalyst in a number of a which have a total weight of b are packed into a stainless steel cylindrical container with an inside diameter of 3 cm and a length of 5 m placed perpendicularly to the horizontal direction, from the upper part of the container, and after the packing by dropping, the number (c) and the total weight (d) of pieces non-passable through a 14-mesh sieve, among pieces of the catalyst recovered from the bottom of the container are measured, and the rate of pulverization by dropping and the rate of shape change are calculated according to the following equations:

$$\text{Rate of pulverization by dropping (\%)} = \frac{b-d}{b} \times 100 \quad \text{Equation I}$$

$$\text{Rate of shape change (\%)} = \frac{\left[\frac{b}{a} - \frac{d}{c}\right]}{\frac{b}{a}} \times 100 \quad \text{Equation II}$$

Example 1

Catalyst powder having the following composition was prepared:

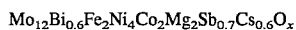

$Mo_{12}Bi_{0.6}Fe_2Ni_4Co_2Mg_2Sb_{0.7}Cs_{0.6}O_x$ wherein Mo, Bi, Fe, Ni, Co, Mg, Sb, Cs and O denote molybdenum, bismuth, iron, nickel, cobalt, magnesium, antimony, cesium and oxygen, respectively; the figures on the lower right of the symbols of element are atomic ratio values for the individual elements; and x is a number of oxygen atoms which is necessary for giving the above valences of the individual constituents.

With 3 parts of graphite powder was thoroughly mixed 97 parts of the catalyst powder obtained, after which the resulting mixture was molded into tablets having a cylindrical shape with an outside diameter of 5 mm, and inside diameter of 2 mm and a height of 2 mm.

Separately, 40 parts of a poly-α-methylstyrene was dissolved in 160 parts of toluene, followed by sufficient stirring (solution A).

In the solution A was immersed 100 parts of the molded catalyst obtained in the above, at room temperature for 1 hour, and then the solution was well drained off the molded catalyst, after which the molded catalyst was dried at 135° C. for 10 hours to evaporate the solvent completely. The weight of the coated catalyst thus obtained was 104.3 parts. The coated catalyst was packed into a fixed-bed flow reactor and treated at 380° C. for 3 hours while introducing nitrogen and then at 380° C. for 3 hours while introducing air. Subsequently, a mixed gas consisting of 5% of isobutylene, 12% of oxygen, 10% of water vapor and 73% of nitrogen (% by volume) was introduced at a reaction temperature of 360° C. for a contact time of 3.6 seconds. The product was collected and analyzed by a gas chromatography to find that the conversion of isobutylene was 92.1%, the selectivity of methacrolein 85.0% and the selectivity of methacrylic acid 4.8%. The conversion of isobutylene and the selectivities of methacrolein and methacrylic acid are defined as follows:

$$\text{Conversion of isobutylene (\%)} = \frac{\text{Number of moles of isobutylene reacted}}{\text{Number of moles of isobutylene fed}} \times 100$$

$$\text{Selectivity of methacrolein (\%)} = \frac{\text{Number of moles of methacrolein produced}}{\text{Number of moles of isobutylene reacted}} \times 100$$

$$\text{Selectivity of methacrylic acid (\%)} = \frac{\text{Number of moles of methacrylic acid produced}}{\text{Number of moles of isobutylene reacted}} \times 100$$

Using 50 g of the coated catalyst of the present invention, its rate of pulverization by dropping and rate of shape change were measured to be 0.7% and 2.3%, respectively.

Comparative Example 1

When a molded catalyst obtained in the same manner as in Example 1 was packed into a reactor without coating with a poly-α-methylstyrene, by a careful handling so as not to cause pulverization, and oxidation reaction of isobutylene was carried out in the same manner as in Example 1, the conversion of isobutylene was 92.1%, the selectivity of methacrolein 85.0% and the selectivity of methacrylic acid 4.8%, namely, the reaction results were not different from those obtained when the coating treatment was carried out. The rate of pulverization by dropping and the rate of shape change were measured to be 5.1% and 22.4%, respectively, that is, the strength was much lower than that attained when the coating treatment was carried out. Accordingly, when the catalyst which has not been subjected to the coating treatment is packed into a large-sized reactor as an industrial catalyst, a considerable amount of the catalyst is pulverized or disintegrated, resulting in an increased pressure loss and a lowered productivity per unit amount.

Comparative Example 2

A coated catalyst was obtained in the same manner as in Example 1 except for using a polymethyl acrylate in place of the poly-α-methylstyrene. The weight of the coated catalyst obtained was 104.3 parts. When the coated catalyst was packed into a fixed-bed flow reactor and heat-treated in the same manner as in Example 1 and the reaction was carried out in the same manner as in Example 1, the conversion of isobutylene was 32.4%, the selectivity of methacrolein 84.6% and the selectivity of methacrylic acid 4.0%, namely, the catalyst had a very low activity. That is, the removal of the polymethyl acrylate by the heat treatment was not complete because of its low depolymerizability.

Comparative Example 3

When the process of Comparative Example 2 was repeated except for changing the heat treatment temperature from 380° C. to 480° C., the catalyst in the reactor generated heat immediately after changing the introduced gas to air, so that the temperature of the catalyst layer rose to 540° C. temporarily. When the reaction was then carried out in the same manner as in Comparative Example 2, the conversion of isobutylene was 74.5%, the selectivity of methacrolein 77.1% and the selectivity of methacrylic acid 2.8%, namely, the catalyst had a very low capability.

Example 2

Catalyst powder having the following composition was prepared:

$$Mo_{12}Bi_{0.8}Fe_3Ni_7Mg_1Mn_{0.3}B_{0.2}Te_{0.1}Si_{0.4}K_{0.1}Cs_{0.3}O_x$$

wherein Mo, Bi, Fe, Ni, Mg, Mn, B, Te, Si, K, Cs and O denote molybdenum, bismuth, iron, nickel, magnesium, manganese, boron, tellurium, silicon, potassium, cesium and oxygen, respectively; the figures on the lower right of the symbols of element are atomic ratio values for the individual elements; and x is a number of oxygen atoms which is necessary for giving the above valences of the individual constituents.

On 80 parts of a spherical silica carrier with a diameter of 3.5 mm was supported 20 parts of the catalyst powder obtained. Separately, 22 parts of a polystyrene was dissolved in 178 parts of ethyl methyl ketone, followed by sufficient stirring (solution A).

To 100 parts of the supported catalyst obtained in the above was adhered 20 parts of the solution A in the form of spray, after which the supported catalyst was dried at 135° C. for 10 hours to evaporate the solvent completely. The weight of the coated catalyst thus obtained was 103.7 parts. Using 50 g of the coated catalyst, its rate of pulverization by dropping was measured to be 0.1%.

Comparative Example 4

Using a supported catalyst obtained in the same manner as in Example 2, as it was without coating with a polystyrene, its rate of pulverization by dropping was measured in the same manner as in Example 2 to be 1.8%.

Example 3

Catalyst powder having the following composition was prepared:

$$Mo_{12}Bi_1Fe_{3.1}Co_3Ni_3Mg_1Pb_1W_{0.1}Ge_{0.1}Sb_{0.8}Cs_{0.3}Tl_{0.3}O_x$$

wherein Mo, Bi, Fe, Co, Ni, Mg, Pb, W, Ge, Sb, Cs, Tl and O denote molybdenum, bismuth, iron, cobalt, nickel, magnesium, lead, tungsten, germanium, antimony, cesium, thallium and oxygen, respectively; the figures on the lower right of the symbols of element are atomic ratio values for the individual elements; and x is a number of oxygen atoms which is necessary for giving the above valences of the individual constituents.

A small amount of water was added to the catalyst powder obtained, and thoroughly mixed therewith, after which the resulting mixture was formed into a columnar shape with a diameter of 3 mm and a height of 5 mm by the use of an extruder and then dried at 110° C. for 10 hours.

Separately, 32 parts of a polymethyl methacrylate was dissolved in 168 parts of acetone, followed by sufficient stirring (solution A).

In the solution A was immersed 100 parts of the supported catalyst obtained in the above, at room temperature for 15 minutes, and then the solution was well drained off the supported catalyst, after which the supported catalyst was dried at 110° C. for 8 hours to evaporate the solvent completely. The weight of the coated catalyst thus obtained was 103.9 parts. Using 50 g of the coated catalyst, its rate of pulverization by dropping and rate of shape change were measured to be 0.2% and 1.2%, respectively.

Comparative Example 5

Using a molded catalyst obtained in the same manner as in Example 3, as it was without coating with a polymethyl methacrylate, its rate of pulverization by dropping and rate of shape change were measured to be 1.5% and 6.9%, respectively.

Example 4

Catalyst powder having the following composition was prepared:

$$Mo_{12}Bi_{1.2}Fe_{2.5}Co_4Ni_3Zn_1Sn_{0.2}P_{0.05}Se_{0.1}Cs_{0.45}O_x$$

wherein Mo, Bi, Fe, Co, Ni, Zn, Sn, P, Se, Cs and O denote molybdenum, bismuth, iron, cobalt, nickel, zinc, tin, phosphorus, selenium, cesium and oxygen, respectively; the figures on the lower right of the symbols of element are atomic ratio values for the individual elements; and x is a number of oxygen atoms which is necessary for giving the above valences of the individual constituents.

A small amount of water was added to the catalyst powder obtained, and thoroughly mixed therewith, after which the resulting mixture was formed into a cylindrical shape with an outside diameter of 5 mm, an inside diameter of 2 mm and a height of 6 mm by the use of an extruder and then dried at 120° C. for 12 hours.

Separately, 28 parts of a polyisobutyl methacrylate was dissolved in 172 parts of acetone, followed by sufficient stirring (solution A).

In the solution A was immersed 100 parts of the molded catalyst obtained in the above, at room temperature for 20 minutes, and then the solution was well drained off the molded catalyst, after which the molded catalyst was dried at 120° C. for 8 hours to evaporate the solvent completely. The weight of the coated catalyst thus obtained was 103.6 parts. Using 50 g of the coated catalyst, its rate of pulverization by dropping and rate of shape change were measured to be 0.4% and 2.1%, respectively.

Comparative Example 6

Using a molded catalyst obtained in the same manner as in Example 4, as it was without coating with a polyisobutyl methacrylate, its rate of pulverization by dropping and rate of shape change were measured to be 2.1% and 9.2%, respectively.

Example 5

Catalyst powder having the following composition was prepared:

$$Mo_{12}Bi_1Fe_{2.2}Co_6Rb_{0.4}O_x$$

wherein Mo, Bi, Fe, Co, Rb and O denote molybdenum, bismuth, iron, cobalt, rubidium and oxygen, respectively; the figures on the lower right of the symbols of element are atomic ratio values for the individual elements; and x is a number of oxygen atoms which is necessary for giving the above valences of the individual constituents.

With 3 parts of graphite powder was thoroughly mixed 97 parts of the catalyst powder obtained, after which the resulting mixture was molded into tablets having a columnar shape with a diameter of 5 mm and a height of 3 mm.

Separately, 30 parts of a polymethyl methacrylate was dissolved in 170 parts of acetone, followed by sufficient stirring (solution A).

In the solution A was immersed 100 parts of the molded catalyst obtained in the above, at room temperature for 20 minutes, and then the solution was well drained off the molded catalyst, after which the molded catalyst was dried at 135° C. for 10 hours to evaporate the solvent completely. The weight of the coated catalyst thus obtained was 104.3 parts. Using 50 g of the coated catalyst, its rate of pulverization by dropping and rate of shape change were measured to be 0.2% and 1.2%, respectively.

Comparative Example 7

Using a molded catalyst obtained in the same manner as in Example 5, as it was without coating with a polymethyl methacrylate, its rate of pulverization by dropping and rate of shape change were measured in the same manner as in Example 5 to be 2.4% and 11.8%, respectively.

INDUSTRIAL APPLICABILITY

The catalyst of the present invention has an excellent mechanical strength, is highly resistant to physical impacts, and very rarely undergoes pulverization and disintegration. Therefore, handling of the catalyst is very easy during its transportation and packing into a reactor. In addition, since its rate of pulverization at the time of packing is low, the catalyst is effective in that the pressure loss at the time of the reaction is small, so that the productivity of the desired products per unit of the catalyst packed is high.

We claim:

1. A molded catalyst or a supported catalyst useful for synthesizing methacrolein and methacrylic acid by vapor phase catalytic oxidation of isobutylene or tertiary butanol with molecular oxygen, the catalyst comprising at least molybdenum, bismuth, iron and oxygen, the catalyst being prepared by coating a molded catalyst or a supported catalyst with one or more highly depolymerizable organic high-molecular weight compounds in a solvent; removing the solvent to dry and to increase the mechanical strength of the coated catalyst; packing a reactor with the coated and dried catalyst; and then subjecting the packed catalyst to a heat treatment at a temperature of lower than 400° C. before the initiation of the reaction for synthesizing methacrolein and methacrylic acid.

2. A catalyst according to claim 1 wherein the organic high-molecular weight compounds have a reduction-by-half temperature for thermal decomposition in a vacuum that is lower than 400° C., and the monomer yield in this case is 30% or more.

3. A catalyst according to claim 1 wherein the amount of said organic high-molecular weight compounds is from 0.1 to 40% by weight based on the weight of said molded catalyst or said supported catalyst.

4. A catalyst according to claim 1 wherein the molded catalyst or the supported catalyst has a composition represented by the general formula:

$$Mo_aBi_bFe_cA_dX_eY_fZ_gO_h$$

wherein Mo, Bi, Fe and O denote molybdenum, bismuth, iron and oxygen, respectively; A denotes nickel and/or cobalt; X denotes at least one element selected from the group consisting of magnesium, zinc, manganese, tin and lead; Y denotes at least one element selected from the group consisting of phosphorus, boron, sulfur, tellurium, silicon, selenium, germanium, tungsten and antimony; Z denotes at least one element selected from the group consisting of potassium, sodium, cesium, rubidium, and thallium; and a, b, c, d, e, f, and g denote atomic ratio values for the individual elements: in the case of a being 12, $0.1 \leq b \leq 5$, $0.1 \leq c \leq 5$, $1 \leq d \leq 12$, $0 \leq e \leq 5$, $0 \leq f \leq 5$, $0.01 \leq g \leq 3$; and h is a number of oxygen atoms which is necessary for giving the above valences of the individual constituents.

5. A process comprising:

packing a reactor with a molded and dried catalyst or a supported and dried catalyst which comprises at least molybdenum, bismuth, and iron, and in which a surface of at least a portion of the molded and dried catalyst or the supported and dried catalyst that has been coated with one or more highly depolymerizable organic high-molecular weight compounds in an amount of 0.1 to 40% by weight based on the weight of the catalyst; and depolymerizing the highly depolymerizable organic high-molecular weight compounds on said catalyst by burning off.

6. A process according to claim 5, wherein the burning off of the organic high-molecular weight compounds is carried out at a temperature of lower than 400° C.

7. A process for producing a molded catalyst or a supported catalyst useful for synthesizing methacrolein and methacrylic acid by vapor phase catalytic oxidation of isobutylene or tertiary butanol with molecular oxygen which comprises spraying a solution of one or more highly depolymerizable organic high-molecular weight compounds in a solvent on a molded catalyst or a supported catalyst comprising at least molybdenum, bismuth, iron and oxygen; removing the solvent to dry and to increase the mechanical strength of the sprayed catalyst; packing a reactor with the dried catalyst; and then removing the organic high-molecular weight compound from the packed catalyst by burning off before the initiation of the reaction for synthesizing methacrolein and methacrylic acid.

8. A process for producing a molded catalyst or a supported catalyst useful for synthesizing methacrolein and methacrylic acid by vapor phase catalytic oxidation of isobutylene or tertiary butanol with molecular oxygen which comprises immersing a molded catalyst or a supported catalyst comprising at least molybdenum, bismuth, iron and oxygen, in a solution of one or more highly depolymerizable organic high-molecular weight compounds in a solvent; removing the solvent to dry and to increase the mechanical strength of the immersed catalyst; packing a reactor with the dried catalyst; and then removing the organic high-molecular weight compound from the packed catalyst by burning off before the initiation of the reaction for synthesizing methacrolein and methacrylic acid.

9. A process according to claim 7, wherein the burning off of the organic high-molecular weight compounds is carried out at a temperature of lower than 400° C.

10. A process according to claim 8, wherein the burning off of the organic high-molecular weight compounds is carried out at a temperature of lower than 400° C.

11. A process for synthesizing methacrolein and methacrylic acid that comprises packing a reactor with a molded, dried catalyst or a supported, dried catalyst which comprises at least molybdenum, bismuth and iron and in which the surface of at least a portion of the molded, dried catalyst or the supported, dried catalyst that has been coated with one or more highly depolymerizable organic high-molecular weight compounds in an amount of 0.1 to 40% by weight based on the weight of the catalyst; and subjecting isobutylene or tertiary butanol to vapor phase catalytic oxidation with molecular oxygen by the use of the catalyst which has been freed of the organic high-molecular weight compounds by depolymerization before the initiation of the reaction for synthesizing methacrolein and methacrylic acid.

12. A process according to claim 11, wherein the depolymerization of the organic high-molecular weight compounds is carried out at a temperature of lower than 400° C.

* * * * *